United States Patent [19]

Man

[11] Patent Number: Plant 7,040

[45] Date of Patent: Sep. 19, 1989

[54] DISTINCT VARIETY OF BEGONIA PLANT NAMED MARILLO

[75] Inventor: Jan Man, Lisse, Netherlands

[73] Assignee: Oglevee Ltd., Connellsville, Pa.

[21] Appl. No.: 251,658

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

The new cultivar is generally characterized by compact growth and abundant flowering quality. The dark foliage contrasts nicely with the unique light orange pink (apricot) flower color. The new cultivar has a very good flower response and produces a large number of buds. Bloom is long lasting.

1 Drawing Sheet

BACKGROUND OF THE NEW PLANT

The present invention comprises a new and distinct cultivar of *Begonia*×*hiemalis* known by the varietal name of Marillo. The new cultivar is a selection of a selfing of the cultivar Ilonka (U.S. Plant Pat. No. 6,203). The cultivar has the same habit and growing characteristics as Ilonka. The light orange-pink flower color distinguishes Marillo from the peach color of the cultivar Ilonka.

The new cultivar was discovered in September of 1984 at Limaplant b.v. in Lisse, Holland; was first asexually reproduced by cuttings at Limaplant b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by compact growth and abundant flowering quality. The dark foliage contrasts nicely with the unique light orange pink (apricot) flower color. The new cultivar has a very good flower response and produces a large number of buds. Bloom is long lasting.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 62° F. at night and 68° F. during the day. The plants were potted in July 1987 in a peat-lite mix and fertilized with a mixture of 20N-10P-20K. Color readings were taken indoors under 200 footcandles of cool white fluorescent tubes. Color references are to the R.H.S. Colour Chart of The Royal Horticultural Society of London, unless noted differently.

Botanical classification: *Begonia*×*hiemalis.*

Flower:

*Fully expanded.*—5.5 cm. in diameter; side view: flattened oval appearance.

*Borne.*—Compound dichasium with opposite bracts at the base of each flower cluster characterized by an obtuse base with a slightly undulate margin, and occur at bifurcation of the inflorescence.

*Stems.*—Strong, medium compact stems; average stem width 0.5–1.5 cm.; color yellow-green group 145B.

*Form.*—Double. Each flower generally has 2 sepals, 6 petals, 12 petaloids (each group may vary ±1 structure).

*Permanence.*—Long lasting bloom, generally an individual flower will remain fresh for 2–3 weeks.

Color:

*Tonality from a distance.*—Base hue of orange with pink overtones.

*Front of petals.*—Fully mature and expanded and are characterized by margin with a color red group orange red 33D and the center of the petal being orange red 30D.

*Reverse of petals.*—Fully mature and expanded and are characterized by a margin with a color red group 41D and inner area having slight orange tone.

*Base of petals.*—Yellow orange group 20B.

*Throat.*—None.

*Calyx.*—Consists of 2 sepals (outer floral envelopes). Front of Calyx — Each sepal is orange group 28C, with undertones of yellow. The very base is yellow group 8C. Back of Calyx — This flower part in the bud stage has a yellow base with pale orange margin. In the mature stage the base of the reverse Calyx is yellow-green group 154C. Other comments — With its outer edge containing average tones, flower color tends to be darker at outer edges and move to lighter tone and hues of orange and yellow toward the center. Immature and not fully expanded petals are characterized by a darker hue than the mature flower.

Petals:

*Texture.*—Crepe paper like (gentle crinkles).

*Appearance.*—Oval with color gradient. Outer edge: yellow/orange overtones to yellow attachment.

*Arrangement.*—Semi-double to fully double.

*Persistence.*—Very good flower response, produces high number of buds.

*Fragrance.*—None observed.

Reproductive organs: All reproductive organs have modified into petaloids. Anthers, filament, pollen, style and ovaries could not be observed.

Plant:

*Form.*—Short, compact, internodes (2–3 cm. apart); good basal branching; strong stems give good self-support.

*Growth.*—Very vigorous.

*Height from soil line.*—18–22 cm. in 11 weeks (no pinch, no cyclocel).

*Spread.*—22–26 cm. in 11 weeks (no pinch, no cyclocel.

Foliage:

*Size.*—Average length of 12 cm. and average width of 9 cm., from a leaf 3 nodes up from the base of stem.

*Quantity.*—Very abundant.

*Shape.*—Acute tip with irregularly lobed attachment; edge is slightly doubly serrate.

*Top side.*—Green group 137A; shiny and smooth.

*Underside.*—Green group 138D.

*Ribs and veins.*—Smooth on top side, raised on lower side, lower side veins only area on leaf where visible tricomes (hairs) appear.

*Rib and vein color.*—Top side: yellow-green group 146B; bottom: yellow-green group 146D.

*Margin.*—None.

*Stipules.*—None.

I claim:

1. A new and distinct variety of begonia characterized by its compact growth, abundant flowering, good response, long lasting bloom and unique contrast between dark foliage and light orange pink flower color, as herein shown and described.

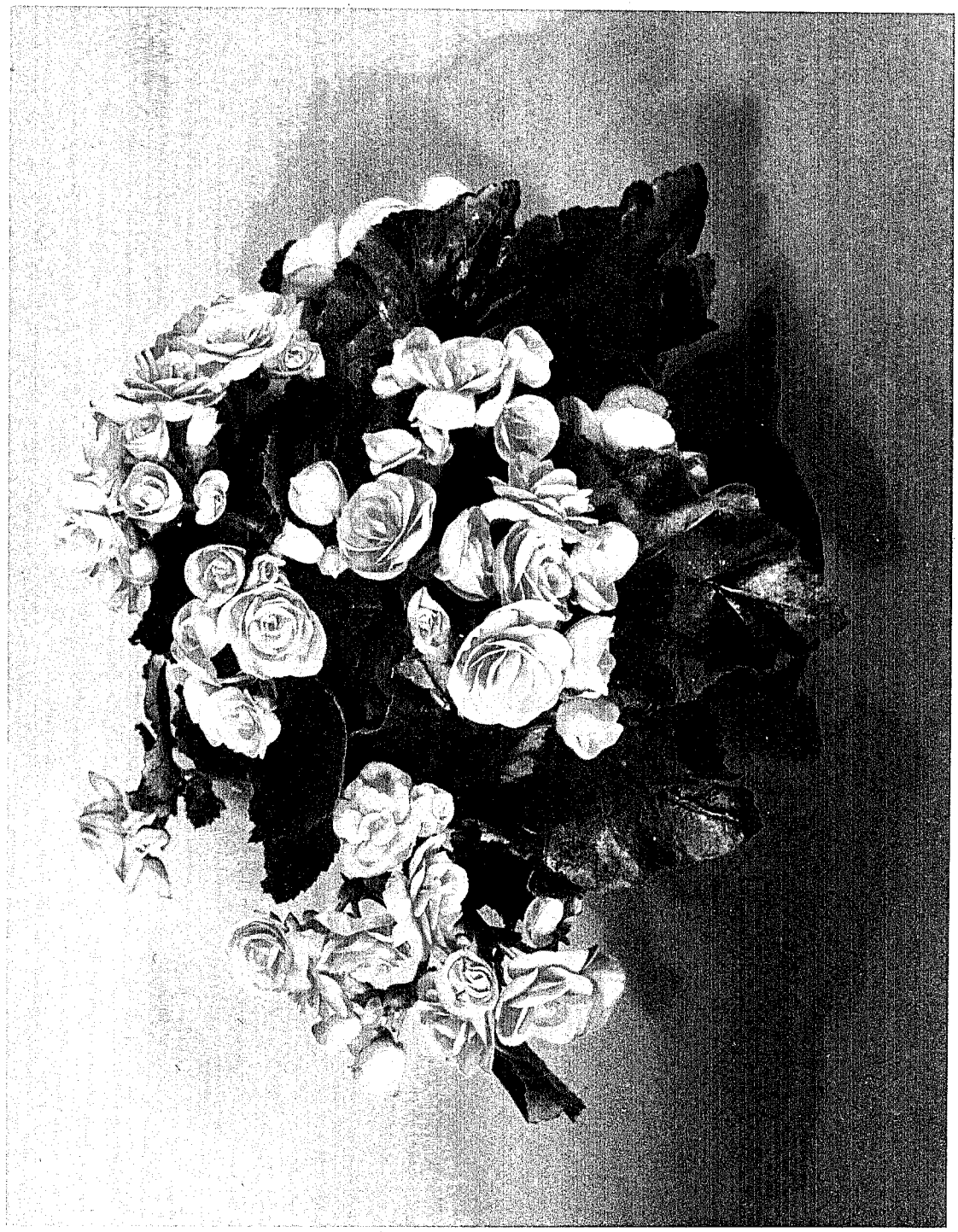

* * * * *